United States Patent [19]

Hassel et al.

[11] Patent Number: 4,841,073

[45] Date of Patent: Jun. 20, 1989

[54] RADICAL ANION SALTS OF DERIVATIVES OF 1,4,5,8-NAPHTHALENETETRACARBOXYLIC ACID AND THEIR USE

[75] Inventors: Tillmann Hassel, Cologne; Jürgen Hocker, Bergisch Gladbach; Gerhard Heywang, Bergisch Gladbach; Hans-Klaus Müller, Bergisch Gladbach; Hans G. Fitzky, Odenthal, all of Fed. Rep. of Germany

[73] Assignee: Bayer Aktiengesellschaft, Leverkusen, Fed. Rep. of Germany

[21] Appl. No.: 928,942

[22] Filed: Nov. 12, 1986

[30] Foreign Application Priority Data

Nov. 30, 1985 [DE] Fed. Rep. of Germany ....... 3542485
Aug. 14, 1986 [DE] Fed. Rep. of Germany ....... 3627667

[51] Int. Cl.$^4$ ............................................. C07D 493/06
[52] U.S. Cl. ..................................... 549/232; 549/231
[58] Field of Search ................... 549/232, 231; 546/66

[56] References Cited

U.S. PATENT DOCUMENTS 4,368,319  1/1983  Hocker et al. .................. 528/352 X

FOREIGN PATENT DOCUMENTS 0224779  6/1987  European Pat. Off. .
2951349  7/1981  Fed. Rep. of Germany .
3000168  7/1981  Fed. Rep. of Germany .

OTHER PUBLICATIONS

Nelson, J. Am. Chem. Soc., vol. 89(23), (1967), pp. 5925–5931.

Primary Examiner—Nicholas S. Rizzo
Assistant Examiner—Andrew G. Rozycki
Attorney, Agent, or Firm—Sprung Horn Kramer & Woods

[57] ABSTRACT

The invention relates to crystalline, stable radical anion salts of derivatives of 1,4,5,8-naphthalenetetracarboxylic acid of the formula

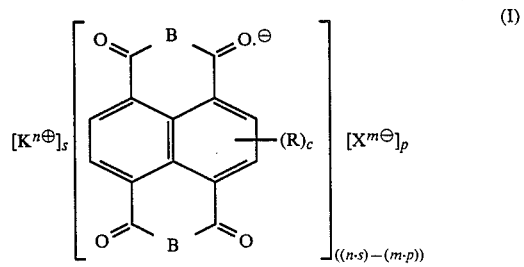

in which p1 k, n, s, x, m, p, B, R and c have the meaning given in the description, to processes for their preparation and to their use as electrically conductive compounds.

8 Claims, No Drawings

RADICAL ANION SALTS OF DERIVATIVES OF 1,4,5,8-NAPHTHALENETETRACARBOXYLIC ACID AND THEIR USE

The invention relates to crystalline, stable radical anion salts of derivatives of 1.4.5.8-naphthalenetetracarboxylic acid, to processes for their preparation and to their use as electrically conductive compounds.

DE-OS (German Offenlegungsschrift) No. 29 51 349 discloses monomeric and DE-OS 30 00 168 (=U.S. Pat. No. 4,368,319) polymeric 1,4,5,8-naphthalenetetracarboxylic acid bis-imides. Although both types of naphthalene-tetracarboxylic bis-imides are described as electrical semi-conductors and, since their electrical conductivity increases upon exposure to light, as photoconductors, it is nonetheless clear from example 4 of DE-OS No. 30 00 168 and from the determination of the direct current conductivities of the preferred naphthalenetetracarboxylic acid bis-imides described in the examples of DE-OS No. 29 51 349 that the direct current conductivity of both monomeric and polymeric 1,4,5,8-naphthalenetetracarboxylic acid bis-imides is only minimal. In example 4, the only example of DE-OS No. 30 00 168 in which any mention is made at all of the direct current conductivity of polymeric naphthalenetetracarboxylic acid bis-imides, a value of $4.2 \times 10^{-8}$ S/cm is given. The determination of the direct current conductivities of the monomeric naphthalenetetracarboxylic acid bis-imides described in the examples produced values of $10^{-14}$ S/cm, $10^{-11}$ S/cm and $9 \times 10^{-7}$ S/cm.

J. Am. Chem. Soc. 89, 5925 (1967) discloses the production of radical anions from 1.4.5.8-naphthalenetetracarboxylic dianhydride and appropriate bis-imides by electrochemical reduction. However, the free radical anions were not isolated in the form of salts, but were prepared only in solution and characterized by ESR spectroscopy.

It has now been found that radical anions of derivatives of 1.4.5.8-naphthalenetetracarboxylic acid can not only be prepared in solution but even be isolated in the form of stable crystalline salts and that these stable crystalline free radical anion salts have a specific direct current conductivity which is higher by orders of magnitude than the specific direct current conductivity of the 1,4,5,8-naphthalenetetracarbonic acid bis-imides which are described in German Offenlegungsschriften Nos. 29 51 349 and 30 00 168. The specific conducttivities of these radical anion salts are between $10^{-5}$ and $10^{-1}$ S/cm. The crystalline radical anion salts of 1.4.5.8-naphthalenetetracarboxylic acid derivatives are, on account of their good electrical conductivity and their, compared with the radical anion salts of 7.7.8.8-tetracyanoquinodimethane (TCNQ), easier accessibility, a new interesting alternative to the TCNQ complexes hitherto used as electrically conductive organic compounds.

The invention therefore relates to crystalline, stable free radical anion salts of the formula

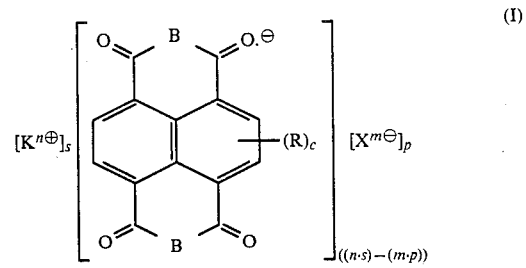

in which
K stands for an n-valent cation,
n is a whole number >0, preferably a whole number from 1 to 5, particularly preferably 1, 2 or 3,
s is a whole number from 1 to 5,
X stands for an m-valent anion;
m is a whole number >0, preferably 1 or 2,
p is 0, 1 or a whole number >1, with the proviso that (m·p) may at most take the value ((n·s)−1);
B stands for oxygen or Y-substituted nitrogen,
Y being an organic radical;
R denotes a substituent and
c is 0 or a whole number from 1 to 4.

If p is a number >1, X can also stand for different anions.

These crystalline stable radical anion salts of the formula (I) can additionally contain uncharged molecules of their parent 1,4,5,8-naphthalenetetracarboxylic acid derivatives and/or solvent molecules. Such free radical anion salts which contain uncharged naphthalenetetracarboxylic acid derivative molecules and/or solvent molecules can be described by the formula

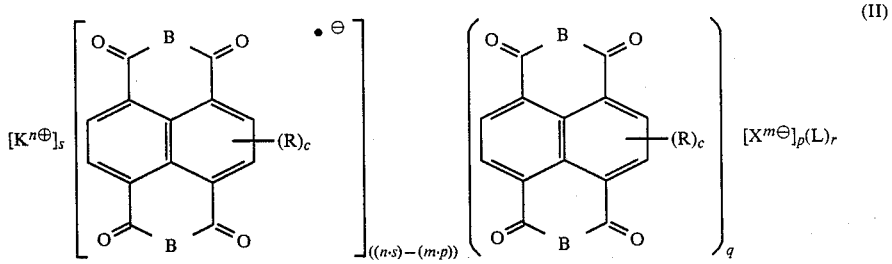

in which
K, n, s, m, p, X, B, R and c have the meaning indicated under the formula (I) and
q stands for 0 or a whole number from 1 to 4
L denotes a solvent molecule and
r stands for 0 or a whole number from 1 to 5.

Suitable cations K are the following types of cations:
1. monovalent and divalent inorganic cations such as the sodium, potassium, rubidium, cesium, calcium, strontium or barium ion,
2. monovalent and multivalent onium ions, as obtained for example by exhaustive alkylation of
    tertiary phosphines such as trimethylphosphine, tributylphosphine and triphenylphosphine;
    tertiary arsines such as tributylarsine, trimethylarsine and triphenylarsine;

thioethers such as dimethyl sulphide, dipropyl sulphide and diethyl sulphide and also tertiary aliphatic, alicyclic, aromatic and heterocyclic monoamines and polyamines derive.

Examples which may be mentioned of alkylating agents for the exhaustive alkylation are: iodomethane, chloromethane, bromoethane, 1,2-dibromoethane, 1,3-dibromopropane, dimethyl sulphate and diethyl sulphate. The preferred alkylating agent is dimethyl sulphate. Preferred cations are the monoammonium and polyammonium cations obtainable by exhaustive alkylation of tertiary monoamines and polyamines.

Suitable tertiary mono- and polyamines which can be used are aliphatic amines such as N.N.N'.N'-tetramethyl-1.2-diaminoethane, N.N.N'.N'-tetramethyl-1.3-diaminopropane, N.N.N'.N'-tetramethyl-1.4-diaminobutane, N.N.N'.N'-tetramethyl-1,6-diaminohexane, N.N.N'.N".N".-pentamethyl-1.5-diamino-3-azapentane and N.N.N'.N".N"-pentamethyl-1.7-diamino-4-azaheptane alicyclic amines such as N.N'-dimethylpiperazine and 1.4-diaza-[2.2,2]-bicyclooctane aromatic amines such as dimethylaniline, N.N.N'.N'-tetramethyl-4.4'-diaminodiphenyl heterocyclic amines such as pyridine, lutidine, collidine, quinoline and isoquinoline.

Preferred tertiary amines are N.N.N'.N'-tetramethyldiaminoethane, N.N.N'.N'-tetramethyl-1.3-diaminopropane, N.N.N'.N'-tetramethyl-1.4-diaminobutane, N.N.N'.N".N"-pentamethyl-1.7-diamino-4-azaheptane, 1.4-diaza-[2.2.2]-bicyclooctane, N.N'-dimethylpiperazine, pyridine and quinoline.

The third type of cation which may be mentioned are carbenium ions as obtained in the oxidation of electron-rich olefines such as tetraaminoethylenes; for example bis-1,3-diphenylimidazolidinylid-2-ene, tetrathioethylene; for example tetrathiafulvalene or diaminodithio(-dioxo)-ethylene; for example bis-3-methylthiazolinylid-2-ene.

The anion X can be monovalent, such as the chloride, bromide, monoethylsulphate, monomethylsulphate, perchlorate, tetrafluoroborate or hexafluorophosphate ion, but also divalent such as the sulphate ion, and trivalent such as the phosphate ion. Preference is given to monovalent anions such as the monomethylsulphate and tetrafluoroborate anion.

The organic radical Y in B can be an optionally substituted alkyl, cycloalkyl, aralkyl or aryl radical; preference is given to $C_1$–$C_6$-alkyl radicals such as the methyl, ethyl, i-propyl, n-butyl and sec.-butyl radical, and also optionally substituted aryl radicals such as phenyl, nitrophenyl, cyanophenyl, halogeno-phenyl, $C_1$–$C_4$-alkoxyphenyl and $C_1$–$C_4$-alkylphenyl radical.

Examples which may be mentioned of the substituent R are halogen atoms such as fluorine, chlorine or bromine; and also nitro, hydroxyl, cyano, $C_1$–$C_4$-alkyl, cyclohexyl, phenyl or carboxylic acid ester groups.

Particular preference is given to those compounds of the formula (I) when in this formula B stands for oxygen or a Y-substituted nitrogen atom, Y being an optionally substituted $C_1$–$C_6$-alkyl radical such as methyl, ethyl, n-propyl, sec.-butyl or n-hexyl radical or a 2-(trimethylammonium-)ethyl, 3-(trimethylammonium)-propyl radical or an optionally monosubstituted or polysubstituted mononuclear aryl radical, such as the phenyl, tolyl, anisyl, dimethylaminophenyl, chloro phenyl, dichlorophenyl, nitrophenyl, cyanophenyl or $C_1$–$C_4$-alkoxycarbonylphenyl radical.

The invention further relates to processes for preparing the crystalline stable radical anion salts of the formula (I) or (II). The processes start from 1.4.5.8-naphthalenetetracarboxylic acid derivatives of the formula

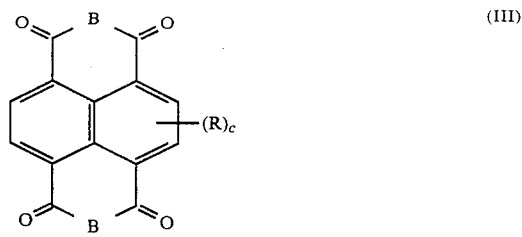

in which

B, R and c have the meaning given under the formula (I).

These derivatives are reduced either chemically or—preferably—electrochemically in an inert organic solvent. The radical anion salts of the formula (I) or (II) obtained in the reduction processes separate out in the form of solid crystallized compounds. These crystalline compounds are separated mechanically from the liquid phase, washed with the solvent used and are dried.

In the electrochemical reduction of the 1.4.5.8-naphthalenetetracarboxylic acid derivatives, the latter are reduced in an inert solvent in the presence of a conducting salt of the formula $$[K^{n\oplus}]_s \, [X^{m\ominus}]_{p'}$$

in which

K, n, s, X and m have the meaning given under the formula (I) and p' is a whole number $>1$, with the proviso that $(n \cdot s) = (m \cdot p)$.

This electrochemical reduction may be illustrated by reference to the following concrete example:

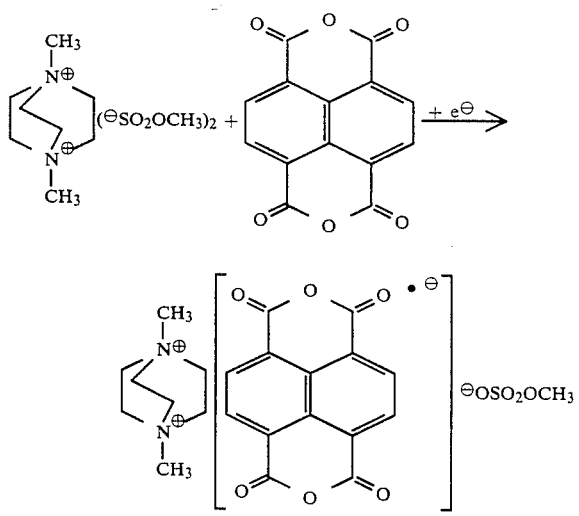

Inert solvents which can be used are:

nitriles such as acetonitrile, propionitrile and butyronitrile amides such as dimethylformamide and dimethylacetamide ureas such as tetramethylurea carbonates such as 1.3-dioxa-cyclohexan-2-one and 1,3-dioxa-4-methyl-cyclopentan-2-one lactones and lactams such as butyrolactone and N-methylpyrrolidone sulphoxides and sulphones such as dimethyl sulphoxide and dimethyl sulphone and tetramethylene sulphone.

Preference is given to nitriles, amides and carbonates such as dimethylformamide, acetonitrile and 1,3-dioxa-cyclohexan-2-one and 1,3-dioxa-4-methylcyclopentan-2-one.

The conducting salts used are the chlorides, bromides, monomethylsulphates, perchlorates, tetrafluoroborates and hexafluorophosphates of the above-mentioned inorganic cations, or the onium salts obtained by exhaustive alkylation of the arsines, phosphines, thioethers and tertiary amines.

These onium salts can be directly used in the form in which they are obtained in the exhaustive alkylation. However, it is also possible first to replace the anion by another anion, for example in tetrabutylammonium chloride the chloride ion by the tetrafluoroborate ion.

Preferred conducting salts are the methosulphates and tetrafluoroborates of the monocations and polycations obtained by exhaustive methylation of N.N.N'.N'-tetramethyl-1,2-diaminoethane, N.N.N'.N'-tetramethyl-1.3-diaminopropane, N.N.N'.N'-tetramethyl-1.4-diaminobutane, N.N.N'.N".N"-pentamethyl-1.7-diamino-4-azaheptane, N,N'-dimethylpiperazine, 1.4-diaza-[2.2.2]-bicyclooctane, pyridine and quinoline.

The electrochemical reduction is carried out at temperatures of $-40°$ C. to the boiling point of the solvent used. Preference is given to temperatures of 40° to 100° C., in particular temperatures of 20° C. to 85° C.

The derivatives of 1.4.5.8-naphthalenetetracarboxylic acid can be used in a concentration of 0.005 mol/l up to the saturation concentration in the particular solvent for the temperature used. Preference is given to concentrations of 0.005 to 0.02 mol/l.

The particular conducting salts can be used in 2- to 20-fold molar excess, relative to tetracarboxylic acid derivative used. Preferably 3 to 12 mol of conducting salt are used per mol of tetracarboxylic acid derivative.

The electrochemical reduction can be carried out potentiostatically or galvanostatically. Preference is given to the galvanostatic method. In a typical galvanostatic experiment, electrolysis is effected in a 100-ml cell with two 16-cm$^2$ Pt electrodes arranged 1 cm apart at a current strength of 2 mA and a cell voltage between 0.7 V and 3 V. Optionally, anode and cathode space can be separated by a membrane or fret.

The radical an ion salts of the formula I according to the invention separate out at the cathode during the electrolysis and can be isolated in an analytically pure form in a manner known per se by mechanical removal, washing with one of the abovementioned inert solvents and drying.

In the chemical reduction, the naphthalenetetracarboxylic acid derivatives are reacted with a chemical reducing agent. Suitable chemical reducing agents are for example inorganic compounds such as alkali metals; preferred reducing agents are organic electron-rich compounds such as, for example, bis-1.3-diphenylimidazolidinylid-2-ene or bis-3-methylbenzothiazolinylid-2-ene. The chemical reaction is preferably carried out in a polar organic solvent such as acetonitrile, dimethylformamide, sulpholane, propylene carbonate or N-methylpyrrolidone.

The chemical reduction is carried out at temperatures of 20° C. to the boiling point of the solvent used. However, by employing pressure it is also possible to use higher reaction temperatures. On cooling down, the semiconducting radical ion salt precipitates in crystalline form.

The radical ion salts of the formulae I and II according to the invention are valuable semiconductors. They find utility for antistatic finishes on plastics and in the electronics sector.

EXAMPLE 1

A heatable 100-ml electrolysis cell with two 16-cm$^2$ Pt electrodes located at a distance of 1 cm away from each other is charged with a solution of 350 mg (1.306 mmol) of 1.4.5.8-naphthalenetetracarboxylic dianhydride and 1.59 g (5 mmol) of N.N.N'.N'-tetramethylpiperazinium bis-tetrafluoroborate in 100 ml of dimethylformamide at 80° C. Electrolysis is effected at 1.5 mA for 26 hours, a cell voltage of 1.4 V becoming established. The radical anion salt crystallizes out at the cathode in the form of bluish-black, metallically shinning needles. They are filtered off with suction, washed with dimethylformamide and then with acetonitrile, and dried.

Yield: 280 mg (=0.4117 mmol=62% of theory) of radical anion salt of the formula

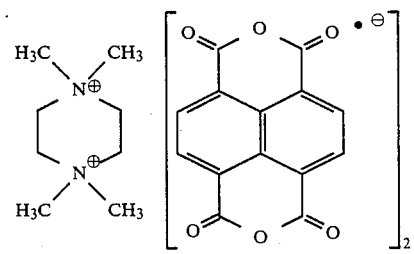

EXAMPLE 2

A heatable 100-ml electrolysis cell with two 16-cm$^2$ Pt electrodes located at a distance of 1 cm away from each other is charged with a solution of 268 mg (1 mmol) of 1.4.5.8-naphthalenetetracarboxylic dianhydride and 3.32 g (9 mmol) of N,N'-dimethyl-diaza-[2.2.2]-bicyclooctane bis-methosulphate in 100 ml of dimethylformamide at 80° C. Electrolysis is effected at 1.5 mA for 26 hours, a cell voltage of 1.5 V becoming estalished. The radical anion salt crystallizes out at the cathode in the form of bluish-black, metallically shining needles. They are filtered off with suction, washed with dimethylformamide and then with acetonitrile, and dried.

Yield: 277 mg (=0.35 mmol=35% of theory) of radical anion salt of the formula

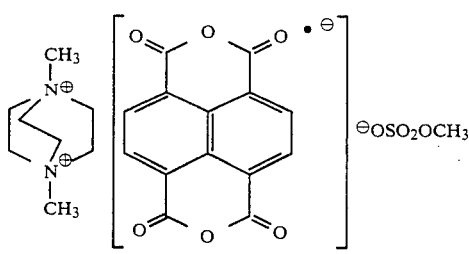

The conductivity of the salt is $4 \times 10^{-3}$ S/cm (powder compact, two-electrode method).

EXAMPLE 3

A heatable 100-ml electrolysis cell with two 16-cm² Pt electrodes located at a distance of 1 cm away from each other is charged with a solution of 0.545 mg (1.3 mmol) of N,N'-diphenylnaphthalenetetracarboxyimide and 2.55 g (10 mmol) of N-methylquinolinium methosulphate in 100 ml of dimethylformamide at 80° C. Electrolysis is effected at 1.5 mA for 13 hours, a cell voltage of 1.35 V becoming established. The radical anion salt crystallizes out at the cathode in the form of bluish-black, metallically shining needles. They are filtered off with suction, washed with dimethylformamide and then with acetonitrile, and dried.

Yield: 140 mg (=0.13 mmol=20% of theory) of radical anion salt of the formula

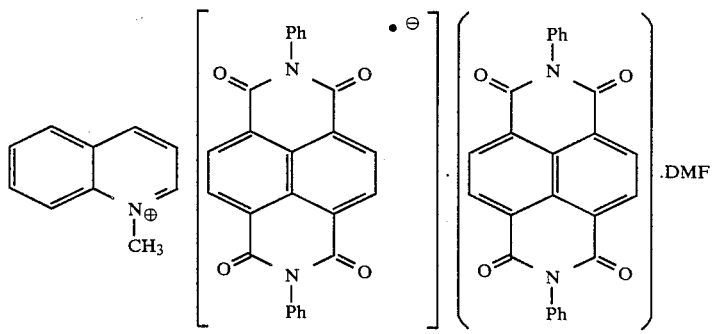

The conductivity of the salt is $6.9 \times 10^{-4}$ S/cm (powder compact, two-electrode method).

EXAMPLE 4

A heatable 100-ml electrolysis cell with two 16-cm² Pt electrodes located at a distance of 1 cm away from each other is charged with a solution of 0.545 mg (1.3 mmol) of N,N'-diphenylnaphthalenetetracarboximide and 1.6 g (5 mmol) of N,N'-dimethyldiaza-[2.2.2]-bicyclooctane bis-tetrafluoroborate in 100 ml of dimethylformamide at 80° C. Electrolysis is effected at 1.5 mA for 8 hours, a cell voltage of 1.4 V becoming established. The radical anion salt crystallizes out at the cathode in the form of bluish-black, metallically shining needles. They are filtered off with suction, washed with dimethylformamide and then with acetonitrile, and dried.

Yield: 176 mg (=0.08 mmol=18% of theory) of radical anion salt of the formula

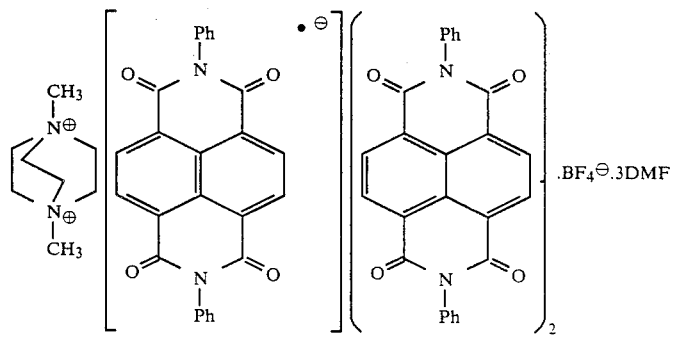

The conductivity of the salt is $4 \times 10^{-4}$ S/cm (powder compact, two-electrode method).

EXAMPLE 5

A heatable 100-ml electrolysis cell with two 16-ccm² Pt electrodes located at a distance of 1 cm away from each other is charged with a solution of 0.545 mg (1.3 mmol) of N,N'-diphenylnaphthalenetetracarboximide and 1.6 g (0.5 mmol) of N,N,N,N',N',N'-hexamethylethylenebisammonium bis-tetrafluoroborate in 100 ml of dimethylformamide at 80° C. Electrolysis is effected at 1.5 mA for 14 hours, a cell voltage of 1.4 V becoming established. The radical anion salt crystallizes out at the cathode in the form of bluish-black, metallically shining needles. They are filtered off with suction, washed with dimethylformamide and then with acetonitrile, and dried.

Yield: 96 mg (=0.05 mmol=15% theory) of radical anion salt of the formula

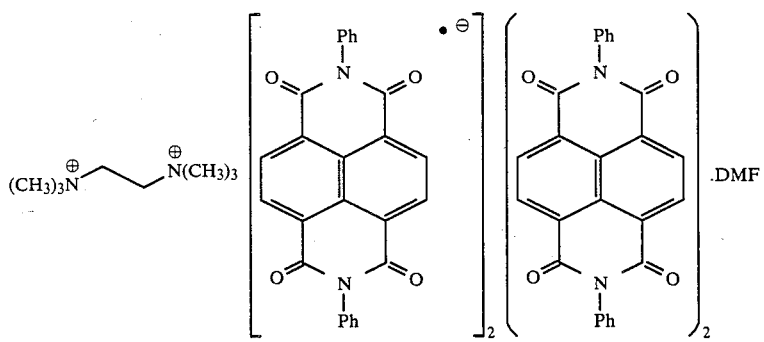

The conductivity of the salt is $7.5 \times 10^{-2}$ S/cm (powder compact, two-electrode method).

EXAMPLES 6 TO 23

The procedure described in Example 1 is followed, except that instead of the conducting salt and solvent used the conducting salts and solvents indicated in the table below were used.

In the table below, the conducting salts, solvents used in Examples 6 to 23 and the resulting radical anion salts of the 1.4.5.8-naphthalenetetracarboxylic acid derivatives have been tabulated.

The radical anion salts obtained are characterized by the formula (II); the table lists the meanings of B, R and X and the values for n, m, p, q, r and c which these assume in the formula (II) for the individual radical anion salts.

The abbreviations used in th table for characterizing the solvents have the following meaning:
DMF dimethylformamide
PPC propylene-1,2-carbonate
AC acetonitrile
NMP N-methylpyrrolidone

TABLE
| Ex. No. | Conducting salt Cation | Anion | Solvent | B | R | c | n | s | ZRA* | q | m | p | X | r |
|---|---|---|---|---|---|---|---|---|---|---|---|---|---|---|
| 6 | 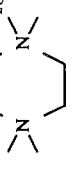 | $(OSO_2OCH_3^{\ominus})_2$ | DMF | oxygen | — | 0 | 2 | 1 | 2 | 0 | — | 0 | — | 0 |
| 7 | 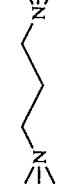 | $(OSO_2OCH_3^{\ominus})_2$ | DMF | oxygen | — | 0 | 2 | 1 | 2 | 0 | — | 0 | — | 0 |
| 8 | 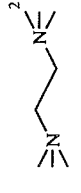 | $(OSO_2OCH_3^{\ominus})_2$ | DMF | oxygen | — | 0 | 2 | 1 | 2 | 0 | — | 0 | — | 0 |
| 9 | 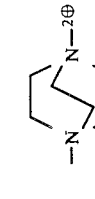 | $(OSO_2OCH_3^{\ominus})_2$ | PPC | oxygen | — | 0 | 2 | 1 | 1 | 0 | 1 | 1 | $OSO_2OCH_3^{\ominus}$ | 0 |
| 10 | 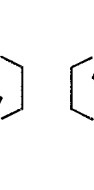 | $(BF_4^{\ominus})_2$ | PPC | oxygen | — | 0 | 2 | 1 | 2 | 0 | — | 0 | — | 0 |
| 11 | 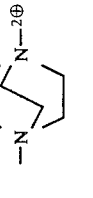 | $(BF_4^{\ominus})_2$ | PPC | oxygen | — | 0 | 2 | 1 | 2 | 0 | — | 0 | — | 0 |
| 12 | 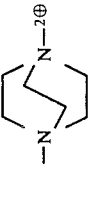 | $(BF_4^{\ominus})_3$ | DMF | oxygen | — | 0 | 3 | 1 | 3 | 0 | — | 0 | — | 0 |
| 13 | 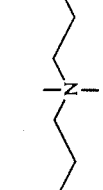 | $(BF_4^{\ominus})_2$ | DMF | oxygen | — | 0 | 2 | 1 | 2 | 0 | — | 0 | — | 0 |
| 14 |  | $(BF_4^{\ominus})_2$ | PPC | oxygen | — | 0 | 2 | 1 | 2 | 0 | — | 0 | — | 0 |

TABLE-continued
| Ex. No. | Conducting salt Cation | Anion | Solvent | B | R | c | n | s | ZRA* | q | m | p | X | r |
|---|---|---|---|---|---|---|---|---|---|---|---|---|---|---|
| 15 | 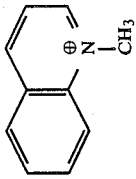 | OSO$_2$OCH$_3$$^\ominus$ | PPC | oxygen | — | 0 | 1 | 1 | 1 | 0 | — | 0 | — | 0 |
| 15 | 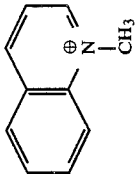 | OSO$_2$OCH$_3$$^\ominus$ | AC | oxygen | — | 0 | 1 | 1 | 1 | 0 | — | 0 | — | 0 |
| 16 | 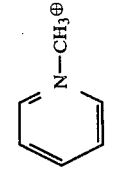 | OSO$_2$OCH$_3$$^\ominus$ | AC | oxygen | — | 0 | 1 | 1 | 1 | 0 | — | 0 | — | 0 |
| 17 | 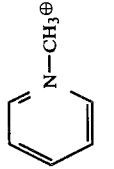 | OSO$_2$OCH$_3$$^\ominus$ | PPC | oxygen | — | 0 | 1 | 1 | 1 | 0 | — | 0 | — | 0 |
| 18 | 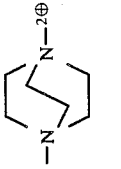 | (BF$_4$$^\ominus$)$_2$ | DMF | N—CH$_3$ | — | 0 | 2 | 1 | 2 | 0 | — | 0 | — | 0 |
| 20 | 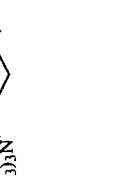 | (BF$_4$$^\ominus$)$_2$ | DMF | 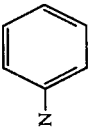 | — | 0 | 2 | 1 | 2 | 2 | — | 0 | — | 0 |
| 21 | 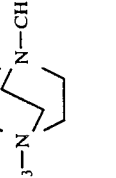 | (OSO$_2$OCH$_3$$^\ominus$)$_2$ | PPC | oxygen | Cl | 4 | 2 | 1 | 2 | 0 | 1 | 1 | OSO$_2$OCH$_3$$^\ominus$ | 2 |

TABLE-continued

| Ex. No. | Conducting salt Cation | Anion | Solvent | B | R | c | n | s | ZRA* | q | m | p | X | r |
|---|---|---|---|---|---|---|---|---|---|---|---|---|---|---|
| 22 | CH₃—N⟨⟩N—CH₃ ²⊕ | (BF₄⊖)₂ | NMP | ⌬–NO₂ (N-phenyl para NO₂) | — | 0 | 2 | 3 | 2 | 0 | 1 | 4 | BF₄⊖ | 0 |
| 23 | CH₃—N⟨⟩N—CH₃ ²⊕ | (BF₄⊖)₂ | PPC | ⌬–Cl (N-phenyl para Cl) | — | 0 | 2 | 3 | 2 | 0 | 1 | 4 | BF₄⊖ | 2 |

*ZRA = (n.s)—(m.p) (= number of radical anions)

EXAMPLE 24

A heatable 100-ml electrolysis cell which is equipped with two 16-cm² platinum electrodes a distance of 1.5 cm apart and whose anode and cathode space are separated from ech other by a fret is charged with a solution of 1.66 g of hexamethylethylenediamine bistetrafluoroborate in 100 ml of diemthylformamide. 0.894 g of N,N'-bis-(3-trimethylammoniumpropyl)-napthalenetetracarboximide bismethosulphate are introduced into the anode space. The solution is heated to 80° C. and, in the course of the heating, is thoroughly flushed with nitrogen. Electrolysis is effected at 1.5 mA for 22 hours; in the course of this period, a cell voltage of 2.0 V becomes established. The radical anion salt crystallizes out at the cathode in the form of brownish-black needle bundles which eventually grow together to form an electrode coating. After the electrolysis has ended, the electrode coating is repeatedly washed with acetonitrile and dried. It has a conductivity of $10^{-5}$ S/cm.

Yield: 0.248 g

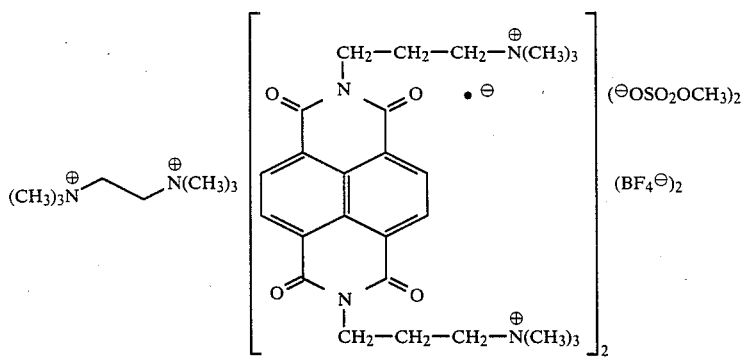

EXAMPLE 25

2.22 g of bis-1.3-diphenylimidazolidinylid-2-ene are dissolved under nitrogen in 50 ml of boiling dimethylformamide and combined with a solution of 4.02 g of naphthalenetetracarboxylic dianhydride in 150 ml of boiling dimethylformamide under nitrogen.

Cooling down leads to the precipitation of 2.25 g of violet-black, metallically shining crystals of the composition:

C=69.3%; H=3.3%; N=4.4%; O=23.0%.

The substance has a specific electric conductivity of $6 \times 10^{-1}$ S/cm.

EXAMPLE 26

The method of Example 25 was used to react 2.8 g of bis-[1,3-(p-dichlorophenyl)-imidazolidinylid-2-ene] with 4.02 g of naphthalenetetracarboxylic dianhydride. 2.4 g of dark-brown crystals having a specific conductivity of $1.2 \times 10^{-4}$ S/cm are obtained.

What is claimed is:

1. A crystalline, stable radical anion salt of the formula

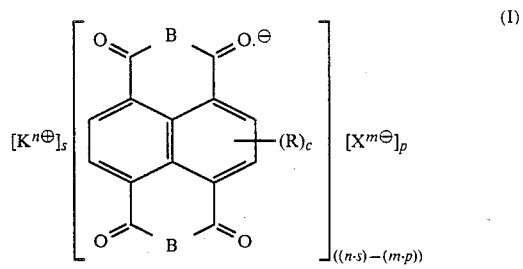

in which
K is an n-valent cation,
n is a whole number $>0$,
s is a whole number from 1 to 5,
X is an m-valent anion,
m is a whole number $>0$,
p is 0, 1 or a whole number $>1$, with the proviso that (m·p) may at most take the value ((n·s)−1);
B is oxygen,
R is halogen, nitro, hydroxyl, cyano, $C_1$–$C_4$-alkyl, cyclohexyl, phenyl, or a carboxylic acid ester and c is 0 or a whole number from 1 to 4.

2. The crystalline, stable radical anion salt of claim 1 wherein
n is a whole number from 1 to 5 and
m is 1 or 2.

3. The crystalline, stable radical anion salt of claim 2 wherein
n is 1, 2 or 3.

4. A radical anion salt of claim 1 which conforms to the formula

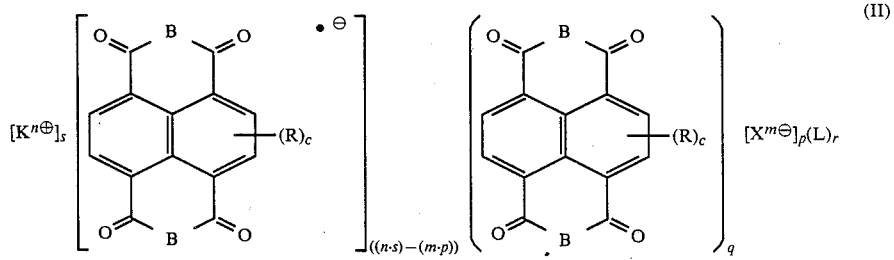

in which

K, n, s, m, p, X, B, R and c have the meaning stated in claim 1 and q stands for 0 or a whole number from 1 to 4

L denotes a solvent molecule and r stands for 0 or a whole number from 1 to 5.

5. A crystalline, stable radical anion salt according to claim 1, wherein said alkyl has 1 to 6 carbon atoms.

6. A crystalline, stable radical anion salt according to claim 1, wherein said halogen for R is selected from the group consisting of fluorine, chlorine and bromine.

7. A crystalline, stable radical anion salt according to claim 1, wherein X is an anion selected from the group consisting of chloride ion, bromide ion, monoethylsulphate ion, monomethylsulphate ion, perchlorate ion, tetrafluoroborate ion, hexafluorophosphate ion, sulphate ion and phosphate ion.

8. A crystalline, stable radical anion salt according to claim 1, wherein R is a cation selected from the group consisting of sodium ion, potassium ion, rubidium ion, cesium ion, calcium ion, strontium ion, barium ion, monovalent onium ions, multivalent onium ions and carbenium ions.

* * * * *

UNITED STATES PATENT AND TRADEMARK OFFICE
CERTIFICATE OF CORRECTION

PATENT NO. : 4,841,073

DATED : June 20, 1989

INVENTOR(S) : Tillmann Hassel, et al

It is certified that error appears in the above-identified patent and that said Letters Patent is hereby corrected as shown below: On the title page:

| | |
|---|---|
| Abstract, line 5 | Delete "pl k" and substitute --K--; same line, delete "x" and substitute --X-- |
| Col. 1, lines 61-62 | Correct spelling of --conductivities-- |
| Col. 5, line 4 | Delete "1.3" and substitute --1,3-- |
| Col. 6, lines 30-31 | Correct spelling of --shining-- |
| Col. 8, line 38 | Delete "16ccm$^2$" and substitute --16-cm$^2$-- |
| Col. 8, line 67 | After "15%" insert --of-- |
| Col. 10, line 24 | Delete "th" and substitute --the-- |
| Col. 15, line 1 under Table | Delete footnote, and substitute --(n·s)-(m·p)(=number of radical anions)-- |
| Col. 17, line 6 | Delete "ech" and substitute --each-- |
| Col. 17, lines 7-8 | Correct spelling of --bistetrafluoroborate-- |
| Col. 17, line 8 | Correct spelling of --dimethylformamide-- |
| Col. 17, line 50 | Delete "10$^{-1}$" and substitute --10$^{-3}$-- |

UNITED STATES PATENT AND TRADEMARK OFFICE
CERTIFICATE OF CORRECTION

PATENT NO. : 4,841,073

DATED : June 20, 1989

INVENTOR(S) : Tillmann Hassel, et al

It is certified that error appears in the above-identified patent and that said Letters Patent is hereby corrected as shown below:

Col. 20, line 6          Delete "R" and substitute --K--

Signed and Sealed this

Seventeenth Day of July, 1990

*Attest:*

HARRY F. MANBECK, JR.

*Attesting Officer*        *Commissioner of Patents and Trademarks*